United States Patent
Ho

(10) Patent No.: US 10,722,055 B2
(45) Date of Patent: Jul. 28, 2020

(54) ADJUSTABLE PILLOW DEVICE AND METHOD

(71) Applicant: David Sai Wah Ho, Hong Kong (CN)

(72) Inventor: David Sai Wah Ho, Hong Kong (CN)

( * ) Notice: Subject to any disclaimer, the term of this patent is extended or adjusted under 35 U.S.C. 154(b) by 360 days.

(21) Appl. No.: 15/517,402

(22) PCT Filed: Aug. 13, 2015

(86) PCT No.: PCT/CN2015/086851
§ 371 (c)(1),
(2) Date: Apr. 6, 2017

(87) PCT Pub. No.: WO2016/054949
PCT Pub. Date: Apr. 14, 2016

(65) Prior Publication Data
US 2017/0238736 A1 Aug. 24, 2017

(30) Foreign Application Priority Data

Oct. 6, 2014 (HK) .................................. 14109930
Feb. 4, 2015 (CN) ......................... 2015 1 0059309

(51) Int. Cl.
*A47G 9/10* (2006.01)
*A61B 5/00* (2006.01)
(Continued)

(52) U.S. Cl.
CPC ............. *A47G 9/1027* (2013.01); *A47G 9/10* (2013.01); *A47G 9/109* (2013.01); *A47G 9/1081* (2013.01);
(Continued)

(58) Field of Classification Search
CPC ...... A47G 9/1027; A47G 9/1036; A47G 9/10; A47G 9/1081; A47G 220/146;
(Continued)

(56) References Cited

U.S. PATENT DOCUMENTS 4,051,917 A * 10/1977 Grundmann ............ F02B 77/13
  181/200
6,951,038 B1 * 10/2005 Ganoe, Sr. ............ A47G 9/1027
  5/636

(Continued)

FOREIGN PATENT DOCUMENTS

CN       1557270       12/2004
CN       1557270 A     12/2004
(Continued)

OTHER PUBLICATIONS

Supplementary European Search Report issued for European Patent Application No. 15848733.0, dated May 28, 2018, 7 pages.
(Continued)

*Primary Examiner* — David R Hare
*Assistant Examiner* — Alexis Felix Lopez
(74) *Attorney, Agent, or Firm* — Hamre, Schumann, Mueller & Larson, P.C.

(57) ABSTRACT

An adjustable pillow device and a pillow adjusting method are disclosed, the adjustable pillow device comprising: a headrest body (1), the height of a region thereof being self-adjustable according to the posture of a sleeper; an inflation/deflation mechanism (2) connected to the headrest body (1) for adjusting the height of a region of the headrest body (1); a sensor (3) for collecting information about the sleeper and providing feedback; a central information processor (4) connected to the sensor (3) and the control end of the inflation/deflation mechanism (2) respectively for receiving information from the sensor (3) and sending an adjustment direction to the control end of the inflation/deflation mechanism (2) according to the sleeping posture information and the body data figure of the sleeper. The adjustable pillow device and method ensure that a sleeper has the most natural and physiologic sleeping posture, and enable automatic adjustment of the head and neck of the (Continued)

sleeper in different sleeping postures to allow the head to be in a proper position relative to the neck, thus providing the sleeper with deeper and longer sleep, improving sleep quality, and meeting the needs of the public.

18 Claims, 12 Drawing Sheets

(51) Int. Cl.
*A61F 5/56* (2006.01)
*A61B 5/024* (2006.01)
*A61B 5/145* (2006.01)

(52) U.S. Cl.
CPC .............. *A61B 5/6887* (2013.01); *A61F 5/56* (2013.01); *A47G 2200/146* (2013.01); *A61B 5/024* (2013.01); *A61B 5/14542* (2013.01)

(58) Field of Classification Search
CPC .. A47G 220/085; A61B 5/6887; A61B 5/024; A61B 5/14542; A61F 5/56
See application file for complete search history.

(56) References Cited

U.S. PATENT DOCUMENTS

| | | | |
|---|---|---|---|
| 8,069,856 B2* | 12/2011 | Kell | A47D 13/08 128/845 |
| 8,503,712 B2* | 8/2013 | Ahmed | A61B 5/14551 382/100 |
| 2005/0050637 A1* | 3/2005 | Graebe | A47G 9/1027 5/644 |
| 2006/0123548 A1* | 6/2006 | Heath | A47G 9/10 5/644 |
| 2007/0240723 A1* | 10/2007 | Hong | A61F 5/56 128/848 |
| 2009/0069642 A1* | 3/2009 | Gao | A61B 5/02055 600/300 |
| 2011/0046498 A1* | 2/2011 | Klap | A61B 5/0205 600/534 |
| 2011/0144455 A1* | 6/2011 | Young | A61B 5/0205 600/301 |
| 2011/0275966 A1* | 11/2011 | Alkhattaf | A47G 9/1027 601/49 |
| 2011/0283460 A1* | 11/2011 | Chan | A47G 9/1027 5/713 |
| 2012/0142999 A1* | 6/2012 | Albu | A47G 9/0215 600/26 |
| 2013/0331661 A1 | 12/2013 | Woodward | |
| 2014/0296747 A1* | 10/2014 | Hermsdorf | A61F 5/56 600/586 |
| 2015/0366368 A1* | 12/2015 | Cheng | A47C 27/081 5/644 |
| 2016/0106225 A1* | 4/2016 | Ham | A47C 27/082 5/655.3 |
| 2017/0238736 A1 | 8/2017 | Ho | |

FOREIGN PATENT DOCUMENTS

| | | |
|---|---|---|
| CN | 200973569 | 11/2007 |
| CN | 102247079 | 11/2011 |
| CN | 202619120 | 12/2012 |
| CN | 103006227 | 4/2013 |
| CN | 104305792 | 1/2015 |
| CN | 104586171 | 5/2015 |
| CN | 204445113 | 7/2015 |
| EP | 1844743 A2 | 10/2007 |
| JP | S6313113 U | 1/1988 |
| JP | 2004223026 | 8/2004 |
| JP | 2005013754 A | 1/2005 |
| JP | 2005066053 A | 3/2005 |
| JP | 2005124609 A | 5/2005 |
| JP | 2007283106 A | 11/2007 |
| JP | 2009106685 A | 5/2009 |
| JP | 2011030634 A | 2/2011 |
| JP | 2011110266 A | 6/2011 |
| JP | 2012170616 A | 9/2012 |
| JP | 2012526593 A | 11/2012 |
| KR | 20060029311 A * | 4/2006 |
| WO | 2005013868 A1 | 2/2005 |
| WO | 2009102968 A1 | 8/2009 |
| WO | 2011057116 | 5/2011 |

OTHER PUBLICATIONS

Office Action issued for Japanese Patent Application No. 2017-519567, dated Aug. 21, 2018, 9 pages including English translation.
First Office Action issued for Australian Patent Application No. 2015330544, dated Dec. 22, 2017, 4 pages.
Second Office Action issued for Australian Patent Application No. 2015330544, dated Jul. 27, 2018, 4 pages.
Office Action issued for Canadian Patent Application No. 2,967,496, dated May 9, 2018, 3 pages.
International Search Report for international appl. No. PCT/CN2015/086851, dated Nov. 17, 2015 (2 pages).
Written Opinion for international appl. No. PCT/CN2015/086851, dated Nov. 17, 2015 (7 pages).
First Office Action issued for Chinese patent appl. No. 201510059309.2, dated Sep. 21, 2015 (30 pages, including English translation).
Second Office Action issued for Chinese patent appl. No. 201510059309.2, dated Apr. 20, 2016 (14 pages, including English translation).
First Office Action issued for Australian Patent Application No. 2018282454, dated Jun. 6, 2019, 5 pages.

* cited by examiner

ADJUSTABLE PILLOW DEVICE AND METHOD

FIELD

The present disclosure relates to the technical filed of health and sleep products, and more particularly, to an adjustable pillow device and method.

BACKGROUND

The quality of sleep of a person determines his/her physical and mental state throughout the day. That makes it particularly important to have a good sleep. A pillow is generally necessary for sleep, and the height and comfort of the pillow have great effects on the quality of sleep. In addition, for office workers who generally sit in an office all day, the pillow is expected to play an important role in the health of the cervical spine during periods of sleep.

Nowadays, a growing number of pillows have a health care function. For example, a "magnetic pillow" has been claimed to have a certain effect on treating neurasthenia, insomnia, headache and tinnitus. A pillow called "cervical pillow" is popular in the U.S. and Hong Kong, which claims to relax muscles of the neck, shoulders and skull base, to eliminate fatigue. In addition, a pillow called "massage pillow" has been developed in Japan, which claims to release energy like an oscillator to promote blood circulation and metabolism, and to have a role in improving sleep. In the history of mankind, there have been many different kinds of pillows and most of them use different contours and shapes or different interior padding materials to achieve different supporting effects. In fact, body figure data varies from person to person. Even within the same person, our skull width, neck width and shoulder width (including fatty tissue); and the special relationship between the back of our skull, cervical spine, and upper back muscle (with fatty tissue) may change from time to time, due to various factor such as age, weight, changes in body size and body/skeletal degeneration. Most, if not all, of the existing pillows belong to a passive device, and such passive pillow cannot satisfy the sleeping needs of all people or of the same person under various times and conditions.

SUMMARY

In view of the above, an objective of the present disclosure is to provide an adjustable pillow device to overcome the defects of the prior art, which enables automatic adjustment of the head and neck of the sleeper according to his/her different sleeping postures, to allow the head to be in a proper position relative to the neck, thus providing the sleeper with deeper and longer sleep, and to improve the quality of sleep.

An adjustable pillow device is provided, including:
a main body, the height of which is adjustable according to the posture of a sleeper;
an inflation-deflation mechanism, connected to the main body, and programmed to perform regional height adjustment of the pillow;
a sensor, programmed to collect and feed back information about the sleeper; and
a central information processor, connected to the sensor and to a control terminal of the inflation-deflation mechanism respectively, and configured to receive the information from the sensor, and send an adjusting direction to the control terminal of the inflation-deflation mechanism based on the sleeping posture information and body figure data of the sleeper.

In one embodiment, the main body includes a cervical spine supporting area and a head supporting area, the cervical spine supporting area has a height higher than the head supporting area, and each of the cervical spine supporting area and the head supporting area is provided with at least one air bag.

In one embodiment, the cervical spine supporting area is provided with three air bags sequentially arranged along the length of the main body, and the head supporting area is provided with one air bag.

In one embodiment, the cervical spine supporting area is provided with three air bags sequentially arranged along the length of the main body, and the head supporting area is provided with three air bags sequentially arranged along the length of the main body.

In one embodiment, the inflation-deflation mechanism includes an air pump, and a pressure tubing connecting the air pump to the air bag, the air pump has a control terminal electrically connected to the central information processor, and the pressure tubing is provided with a switching valve electrically connected to the central information processor.

In one embodiment, the air pump is a silent air pump.

In one embodiment, the cervical spine supporting area and/or the head supporting area are provided with a temperature adjuster.

In one embodiment, the adjustable pillow device further includes plates arranged in the head supporting area and/or the cervical spine supporting area respectively, the plate arranged in the head supporting area is positioned away from the top of the head supporting area, and the plate arranged in the cervical spine supporting area is positioned away from the top of the cervical spine supporting area.

In one embodiment, the central information processor and/or the air pump are arranged in a box with sound insulation properties.

In one embodiment, the adjustable pillow device further includes an information storage device electrically connected to the central information processor.

In one embodiment, the adjustable pillow device further includes an information transmission mechanism electrically connected to the central information processor.

In one embodiment, the adjustable pillow device further includes an environmental information collector electrically connected to the central information processor.

In one embodiment, the sensor includes an image sensor to be installed above the head of a sleeper.

In one embodiment, the sensor includes an accelerometer to be located below the main body or on the chest, back, hip or head of the sleeper.

In one embodiment, the sensor includes an image sensor installed above the head of the sleeper, and an accelerometer located below the main body or on the chest, back, hip or head of the sleeper.

In one embodiment, the sensor further includes a sound sensor.

In one embodiment, the sensor further includes a blood-oxygen measuring device attached to a hand of the sleeper.

A pillow adjusting method is provided, including:
collecting, by a sensor, information about a sleeper;
receiving, by a central information processor, the information from the sensor, and sending an adjusting direction to an inflation-deflation mechanism based on the sleeping posture information and body figure data of the sleeper; and performing, by a main body, regional height adjustment of the main body, driven by the inflation-deflation mechanism.

The pillow adjusting method further includes:

maintaining physiological curvature of the cervical spine of the sleeper by directing the main body to perform regional height adjustment via the inflation-deflation mechanism, when the sensor detects that the sleeper is lying supine.

The pillow adjusting method further includes:

maintaining that an axial line from the sleeper's vertex to the sleeper's chin is on the same horizontal plane as the sleeper's cervical and thoracic spine by directing the main body to perform regional height adjustment via the inflation-deflation mechanism, when the sensor detects that the sleeper is lying laterally.

The pillow adjusting method further includes:

facilitating the sleeper to change from lying supine to lying laterally by directing the main body to perform regional height adjustment via the inflation-deflation mechanism, when the sensor detects that the sleeper is snoring, with a respiratory rate below a predetermined value, and that the sleeper is lying supine.

The pillow adjusting method further includes:

facilitating the sleeper to change from sleeping on his/her left side to sleeping on his/her right side by directing the main body to perform regional height adjustment via the inflation-deflation mechanism, when the sensor detects that the sleeper is snoring, with a respiratory rate below a predetermined value, and that the sleeper is sleeping on his/her left side; and facilitating the sleeper to change from sleeping on his/her right side to sleeping on his/her left side by directing the main body to perform regional height adjustment via the inflation-deflation mechanism, when the sensor detects that the sleeper is snoring, with a respiratory rate below a predetermined value, and that the sleeper is sleeping on his/her right side.

Preferably, the method further includes:

controlling, by the central information processor, the inflation-deflation mechanism to withhold from intervening, when the sensor detects that the sleeper is asleep, and that each of blood oxygen saturation, breathing rate and heart rate of the sleeper falls within a predetermined range.

Advantages or principles of the above technical solutions are described as below.

(1) According to the present disclosure, a sensor is used to collect information about a sleeper, and a central information processor is used to process the sleeping posture information and body figure data of the sleeper, and to direct an inflation-deflation mechanism to control a main body to perform an active adjustment, and in this way, timely adjustment can be achieved, to ensure that the sleeper has a most natural and physiologic sleeping posture.

(2) The present disclosure can ensure the cervical spine is in a resting or recovery state with minimal strain and twist.

(3) The present disclosure can prolong the duration when the sleeper is in deep sleep, and improve blood circulation through the carotid and vertebral arteries.

(4) The present disclosure can reduce the incidence of conscious or subconscious wakening during sleep.

(5) The present disclosure can prolong the duration when the upper airway is patent, reduce snoring, reduce the occurrence of sleep apnea, improve the amount of oxygen carried by red blood cells, and prevent oxygen deficiency from occurring.

(6) The present disclosure can reduce the occurrence of tachycardia, bradycardia or arrhythmia caused by sleep apnea or upper airway obstruction.

(7) The device according to the present disclosure is simple in structure and design, and reliable in posture detection and adjustment, and can meet the public's needs.

DESCRIPTION OF REFERENCE SIGNS

1: main body; 2: inflation-deflation mechanism; 3: sensor; 4: central information processor; 5: pressure tubing; 6: cervical spine supporting area; 7: head supporting area; 8: air bag; 9: plate; 10: image sensor; 11: sound sensor; and 12: accelerometer.

DETAILED DESCRIPTION OF THE PREFERRED EMBODIMENTS

The embodiments of the present disclosure will be described in detail by reference to the accompanying drawings.

Example One

Figure 1:
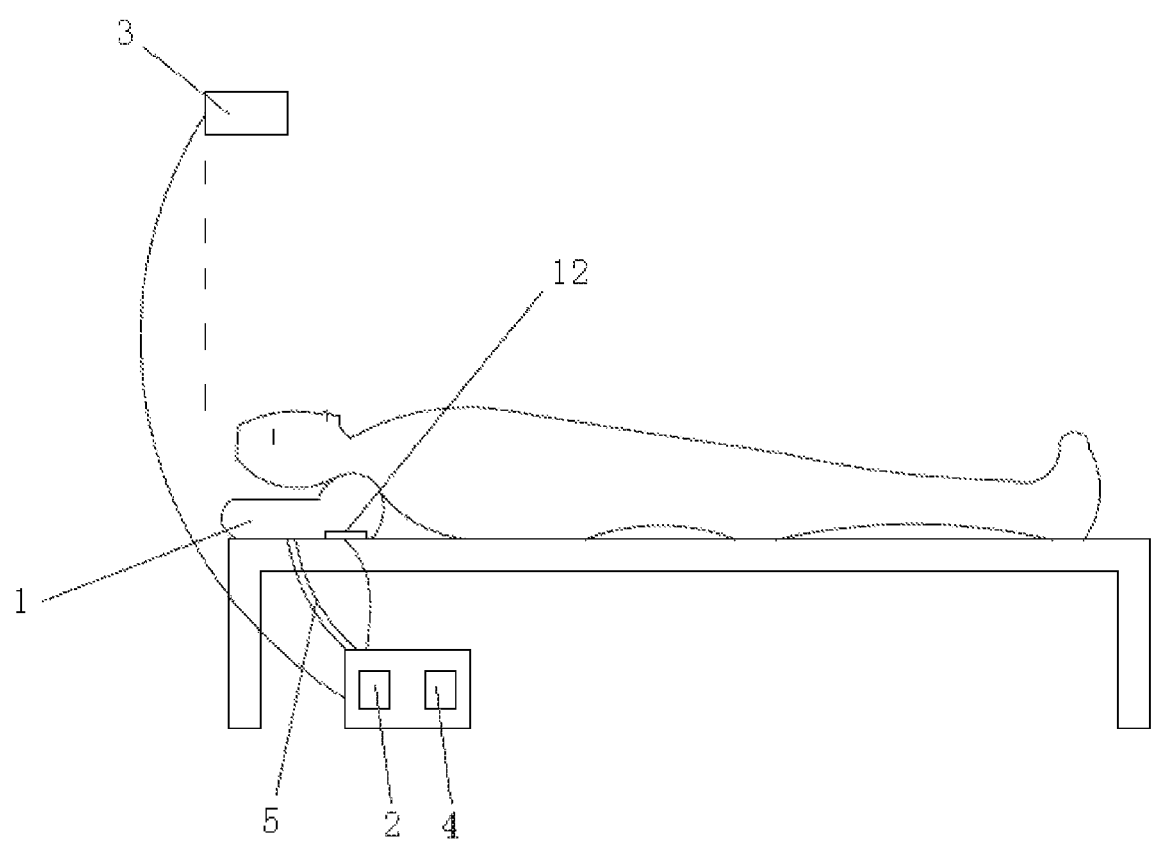
FIG. 1 is a structural schematic diagram illustrating an adjustable pillow device according to Example One of the present disclosure.

As shown in FIG. 1, an adjustable pillow device is provided in this embodiment, including a main body 1, configured to perform regional height adjustment according to the posture of a sleeper; an inflation-deflation mechanism 2, connected to the main body, and programmed to adjust the regional height of the pillow; a sensor 3, programmed to collect and feed back information about the sleeper; and a central information processor 4, connected to the sensor 3 and to a control terminal of the inflation-deflation mechanism 2 respectively, and configured to receive the information from the sensor 3, and send an adjusting direction to the control terminal of the inflation-deflation mechanism 2 based on the sleeping posture information and body figure data of the sleeper. During the sleep monitoring, the central information processor 4 may receive information from the sensor 3, recognize whether the sleeper is lying supine or laterally, and acquire positional information of the head of the sleeper. Every time the sleeper changes his/her position, the sensor 3 may detect the changed posture of the sleeper, and the inflation-deflation mechanism 2 may drive the main body to perform a corresponding adjustment. Various kinds of sensors 3 may be used, as long as these sensors can detect or sense the sleeping posture of the sleeper, collect the detected or sensed information, and feed back the information to the central information processor 4 timely. In addition, the arrangement of the sensor 3 varies with the kind of the sensor 3.

According to the present disclosure, a sensor 3 is used to collect information about a sleeper, and a central information processor is used to process the sleeping posture information and body figure data of the sleeper, and to direct an inflation-deflation mechanism 2 to control a main body 1 to perform an active adjustment. In this way, a purposeful and timely adjustment can be achieved, to ensure that the sleeper has a most natural and physiologic sleeping posture. The present disclosure can also ensure the cervical spine is in a resting or recovery state with minimal strain and twist, increase the period when the sleeper is in deep sleep, improve blood circulation of the carotid and vertebral arteries. The present disclosure can reduce the incidence of conscious or subconscious awakening during sleep, prolonging the duration when the upper airway is unobstructed, to lower noise caused by snoring, reduce snoring, reduce sleep apnea, improve the amount of oxygen carried by red blood cells, and prevent oxygen deficiency from occurring. In addition, the present disclosure can reduce the occurrence of tachycardia, bradycardia or arrhythmia caused by sleep apnea or upper airway obstruction.

Figure 2:
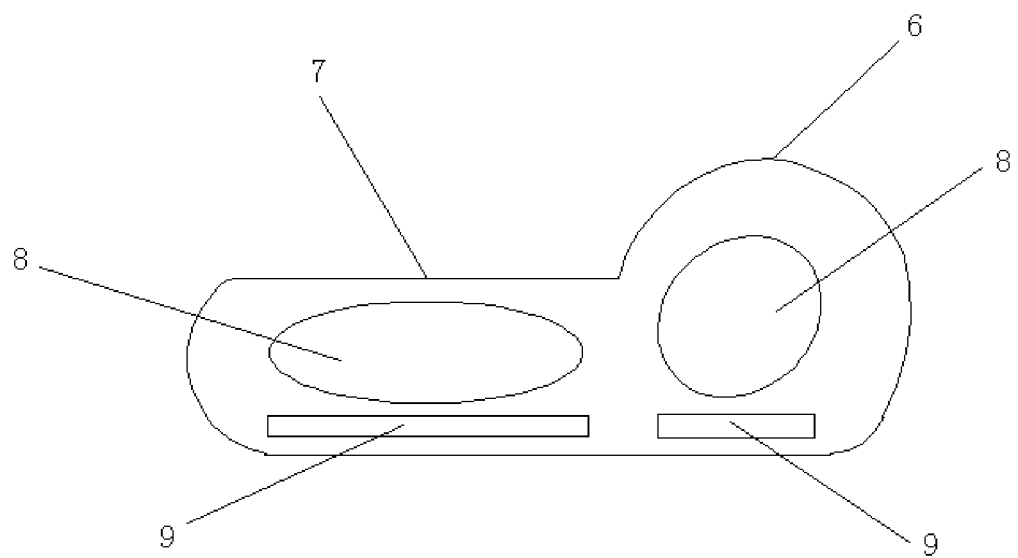
FIG. 2 is a cross-sectional view of a main body according to Example One of the present disclosure.

As shown in FIG. 2, the main body 1 in this embodiment includes a cervical spine supporting area 6 and a head supporting area 7. The cervical spine supporting area 6 has a height higher than the head supporting area 7, facilitating the achievement of a physiological curvature. Each of the cervical spine supporting area 6 and the head supporting area 7 is provided with at least one air bag 8. In this way, the regional heights of the main body 1 may be adjusted by inflating or deflating the air bag 8. In this embodiment, the cervical spine supporting area 6 is provided with three air bags 8 sequentially arranged along the length of the main body 1, improving the sensitivity of the adjustment to the cervical spine. The head supporting area 7 is provided with one air bag 8.

In this embodiment, the inflation-deflation mechanism 2 includes an air pump, and a pressure tubing connecting the air pump to the air bag 8. The air pump has a control terminal electrically connected to the central information processor 4, and the pressure tubing 5 is provided with a switching valve electrically connected to the central information processor 4. The air pump is preferably a silent air pump, to prevent noise generated during the operation of the air pump from affecting the sleep quality of the sleeper. The inflation-deflation mechanism 2 may activate one or more air pumps, and switch on one or more corresponding switching valves to inflate the air bag 8 through the pressure tubing 5, after receiving the direction for adjustment from the central information processor 4, such that the height and contour of the main body can be adjusted. The switching valve may be switched off after the adjustment is completed. Whenever the sensor 3 detects any change in posture of the sleeper, whether the sleeper is lying supine or laterally, the central information processor 4 will direct the air pump to drive different air bags 8, to achieve corresponding height adjustments to the different areas of the main body 1, so that the sleeper is always in a physiologic posture, in which the head and cervical spine are in a perfectly balanced and resting state, with minimal strain and twist, to help improve the sleep quality of the sleeper.

Further, the cervical spine supporting area 6 and/or the head supporting area 7 are provided with a temperature adjuster programmed to fine-tune the temperature of the main body, to help the sleeper to sleep and improve the sleep quality. The temperature adjuster is electrically connected to the central information processor to transmit data about any temperature variation in the main body 1. According to practical requirements, the adjustable pillow device may further include plates 9 arranged in the head supporting area 7 and/or the cervical spine supporting area 6 respectively. The plate 9 arranged in the head supporting area 7 may be positioned away from the top of the head supporting area 7, and the plate 9 arranged in the cervical spine supporting area 6 may be positioned away from the top of the cervical spine supporting area 6, to avoid affecting the flexibility and suppleness of the main body 1. The plates 9 may provide an additional pre-adjustment to the height level of the main body.

As shown in FIG. 1, the central information processor 4 and/or the air pump are arranged in a box with sound insulation properties. The box may be arranged under the main body 1, or placed on the floor, to greatly reduce noise, and avoid heating of any main body components, thereby affecting the sleeper. It will be appreciated that the position of the box is not limited to be arranged under the main body 1, and the box can be arranged at other position according to the shape of the main body 1, for example, the box may be embedded in the main body 1.

In this embodiment, the adjustable pillow device may include an environmental information collector electrically connected to the central information processor. The environmental information collector may be arranged above the main body 1. The environmental information collector is programmed to collect environmental information, such as ambient temperature, humidity, or air quality. The environmental information collector is an optional component.

The adjustable pillow device may further include an information storage device electrically connected to the central information processor 4. Both the sleeping posture and other physiologic information (such as blood oxygen, heart rate, respiratory rate or period of snoring) collected by each sensor 3, and the environmental information (such as ambient temperature, humidity, or air quality) collected by the environmental information collector can be stored in the information storage device. In this embodiment, the information storage device is a storage card.

In this embodiment, the adjustable pillow device may further include an information transmission mechanism electrically connected to the central information processor 4. The sleep information and the environmental information may be transmitted to an electronic device (such as mobile phone, smart bracelet, smart watch or other portable electronic devices) via network, and be displayed on an electronic screen. Any change in sleeping posture, the exact sleeping posture at any given time and the duration of each sleeping posture may be displayed, so that the sleeper may have a clear idea on his/her sleep quality all night. These information on human physiology and sleep quality may be uploaded to any "health" software products or apps embedded in a smart phone (for example, with an Android or iPhone operating system).

Figure 4:
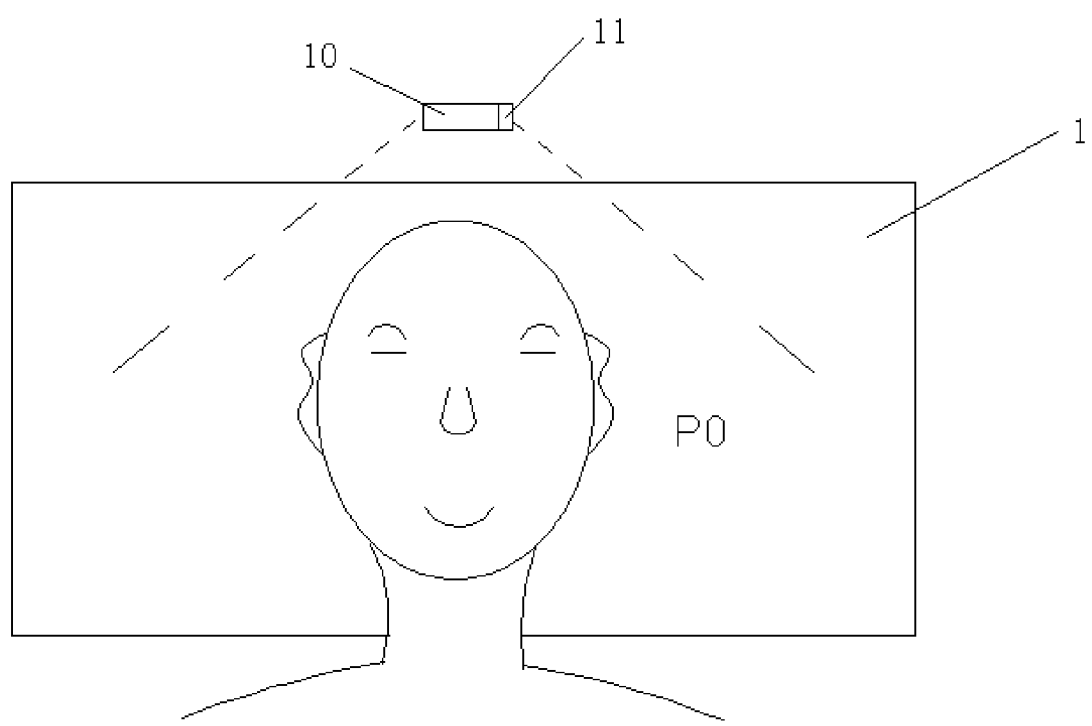
FIG. 4 is a top view showing a sleeper lying supine (P0) according to Example One of the present disclosure.

As shown in FIGS. 1 and 4, the sensor 3 includes an image sensor 10 arranged above the head of the sleeper, programmed to sense the sleeping posture of the sleeper, and transmit information to the central information processor 4 in real time. Preferably, the distance between the image sensor 10 and the main body 1 is within a range of 1 m~2 m, which is a good distance to collect sleep information. In this embodiment, the image sensor 10 is a passive infrared sensor 3 programmed to collect thermal infrared images of the sleeper, and transmit information to the central information processor 4 in real time. The sensor 3 may detect every change in the sleeping posture of the sleeper without emitting any light. Two orthogonal images taken at an angle of 90 degrees between them may be combined to form a "stereoscopic image", to improve the accuracy in the analysis of the posture of the sleeper.

Figure 9A:
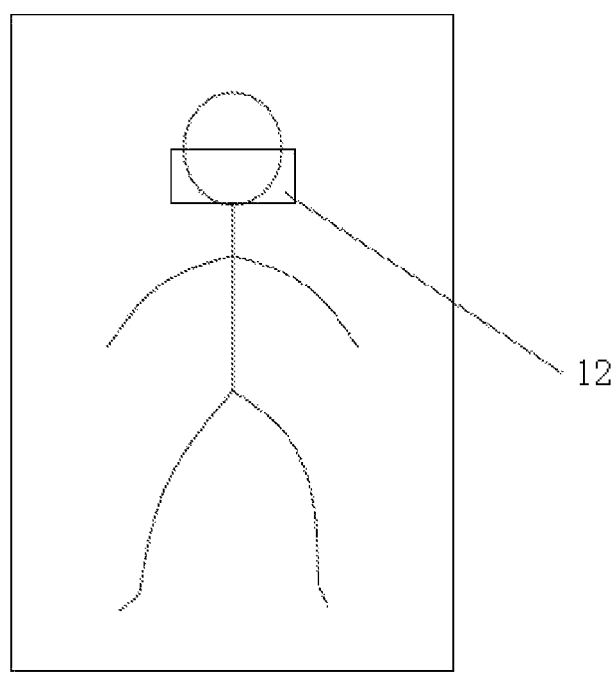
FIG. 9a is a top view showing an accelerometer arranged below the main body according to Example One of the present disclosure.
Figure 9B:
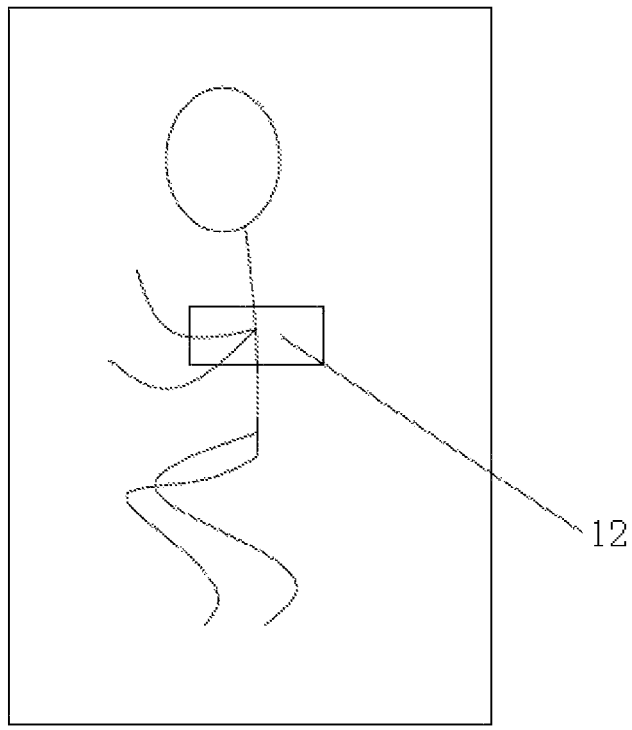
FIG. 9b is a top view showing an accelerometer arranged on the chest or the back of the sleeper according to Example One of the present disclosure.
Figure 9C:
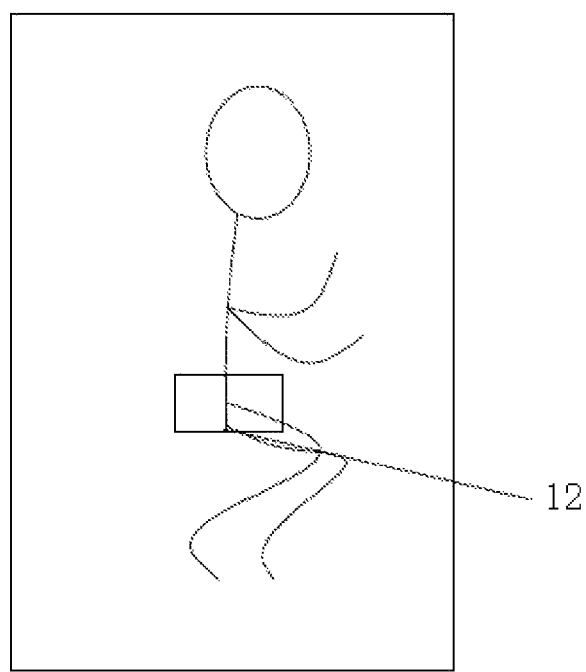
FIG. 9c is a top view showing an accelerometer arranged on the hip of the sleeper according to Example One of the present disclosure.

As shown in FIGS. 9a, 9b and 9c, the sensor 3 may further include an accelerometer 12 arranged below the main body 1 or on the chest, back, hip or head of the sleeper. The accelerometer 12 may detect a change in the gradient every time the sleeper changes his/her sleeping posture. In addition, the accelerometer 12 may also detect the heart rate and respiratory rate of the sleeper, to obtain the sleep information of the sleeper.

In this embodiment, the sensor may further include a sound sensor 11 arranged above the main body 1. The sound sensor 11 is programmed to detect information about any snoring of the sleeper, such as the time of snoring, and transmit the detected information to the central information processor 4 to be analyzed. In this way, the respiratory rate, respiratory pattern and sound of the sleeper may be recorded in real time. The sound sensor 11 is also programmed to detect noise inside or outside the room, such as a sudden noise. The central information processor 4 may record the noise, and show the time of noise, the influence on the sleep quality of the sleeper and so on in terms of diagrams. This may allow the sleeper to identify and avoid certain external factors which may affect his/her sleep quality. If the ambient noise or the time when the sleeper is snoring, does not need to be detected, the sensor 3 does not need to include a sound sensor 11. The sound sensor 11 is an optional component. The sensor 3 may further include a blood-oxygen measuring device attached to a hand of the sleeper, programmed to detect the blood oxygen of the sleeper.

The image sensor 10, the sound sensor 11 and the environmental information collector may be mounted on a wall. For example, they may be fixed on the wall through bolts, nails or other fixing devices respectively, or they be hung on the wall through strings or adhesive devices respectively. In addition, all the sleep information collected by the image sensor 10, the accelerometer 12, the environmental information collector and the sound sensor 11 may be recorded and stored, and transmit to another electronic device via network.

A pillow adjusting method is also provided, including:
collecting, by a sensor 3, information about a sleeper;
receiving, by a central information processor 4, the information from the sensor 3, and sending an adjusting direction to an inflation-deflation mechanism 2 based on the sleeping posture information and body figure data of the sleeper; and
performing, by a main body 1, the regional height adjustment of the main body, driven by the inflation-deflation mechanism 2.

The sleeper will need to enter certain human-body figure data, such as lateral and antero-posterior dimensions of his/her head, neck, chest, and shoulders into the device, before using the adjustable pillow device. The central information processor 4 will store these parameters and work out the best physiological curve based on the above data. Alternatively, the above data may also be detected by the sensor and input into the central information processor 4 automatically. In this way, the sensor 3 may collect information about the sleeper, and the central information processor 4 may process the information and calculate the parameters of the sleeper, to direct the inflation-deflation mechanism 2 to control the main body 1 to have an active adjustment, so that a purposeful and timely adjustment can be achieved, to ensure that the sleeper has a most natural and physiologic sleeping posture.

Figure 3:
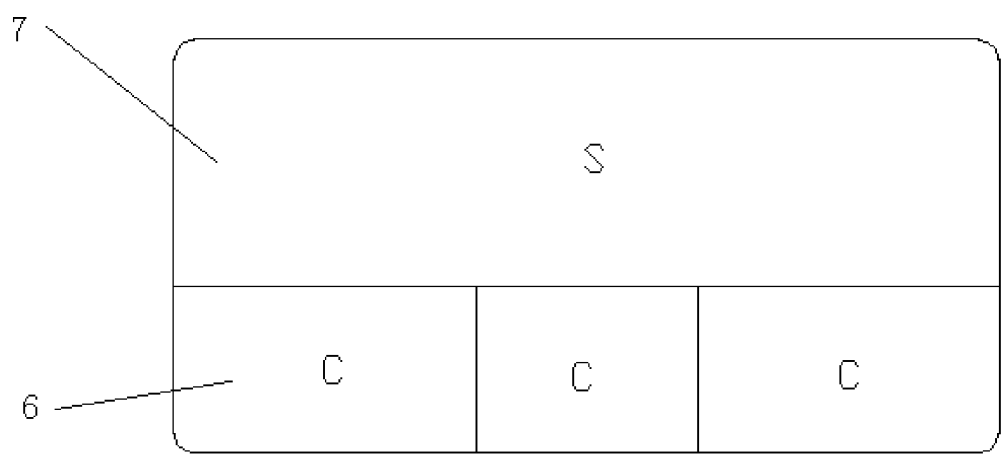
FIG. 3 is a top view of the main body according to Example One of the present disclosure.
Figure 10A:
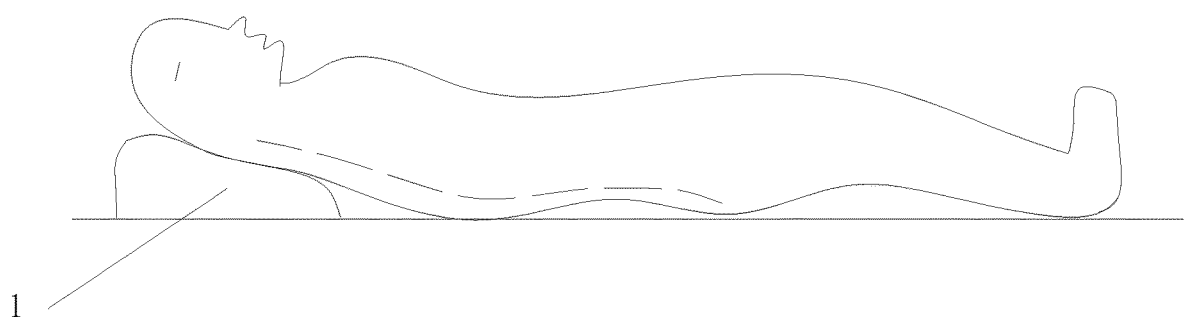
FIG. 10a is a schematic diagram illustrating a sleeper lying supine with too high a head supporting area and too low a cervical spine supporting area according to Example One of the present disclosure.
Figure 10B:
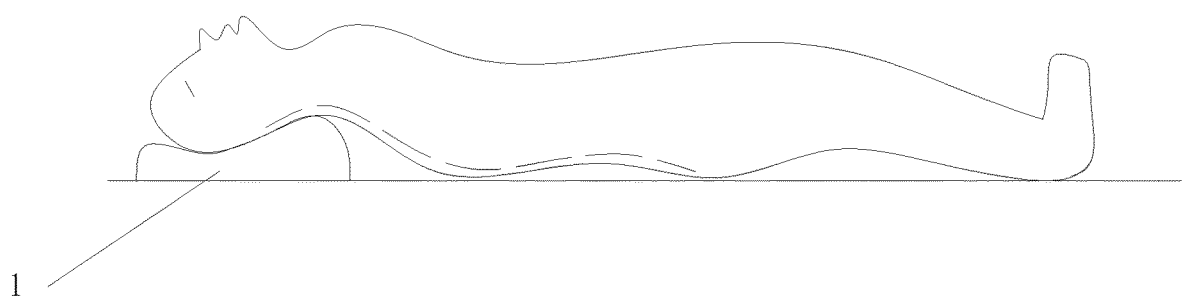
FIG. 10b is a schematic diagram illustrating a sleeper lying supine with too low a head supporting area and too high a cervical spine supporting area according to Example One of the present disclosure.
Figure 10C:
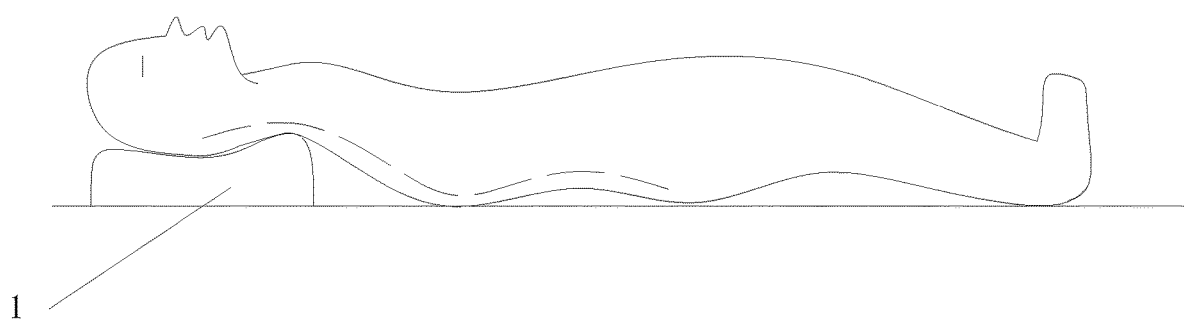
FIG. 10c is a schematic diagram illustrating a sleeper lying supine with a head supporting area and a cervical spine supporting area of appropriate heights according to Example One of the present disclosure.

As shown in FIG. 10a, the head supporting area is too high, and the cervical spine supporting area is too low, so the cervical spine of the sleeper lacks a physiological curve. As shown in FIG. 10b, the head supporting area is too low, and the cervical spine supporting area is too high, so the cervical curvature of the sleeper is too excessive. As shown in FIG. 10c, each of the head supporting area and the cervical spine supporting area has an appropriate height, maintaining the physiological curve of the cervical spine of the sleeper. As shown in FIGS. 3 and 4, when the sensor 3 detects that the sleeper is lying supine, the inflation-deflation mechanism 2 may drive the main body 1 to adjust the heights of the head and neck areas, maintaining the optimal physiological curve of the cervical spine of the sleeper. When the sleeper is lying supine, the accelerometer 12 may detect that the body is sleeping on the back, or the image sensor may sense an infrared image of the front of the person. The image or information collected by the accelerometer 12 may be transmitted to the central information processor 4, to recognize that the head and neck, or the face of the sleeper is in a posture of P0. Pre-entered data about the head, neck, shoulder and chest of the user; data stored after a period of use and adaptation of the user; or personalized and overriding data selected by the user; may be used by the central information processor 4. The central information processor 4 will direct the air bags 8 in area S of the head supporting area 7, and air bags 8 in areas C of the cervical spine supporting area 6 through the air pump and the pressure tubing 5, to inflate or deflate, thereby adjusting the heights of the areas S of the head supporting area 7 and the areas C of the cervical spine supporting area 6.

Figure 5:
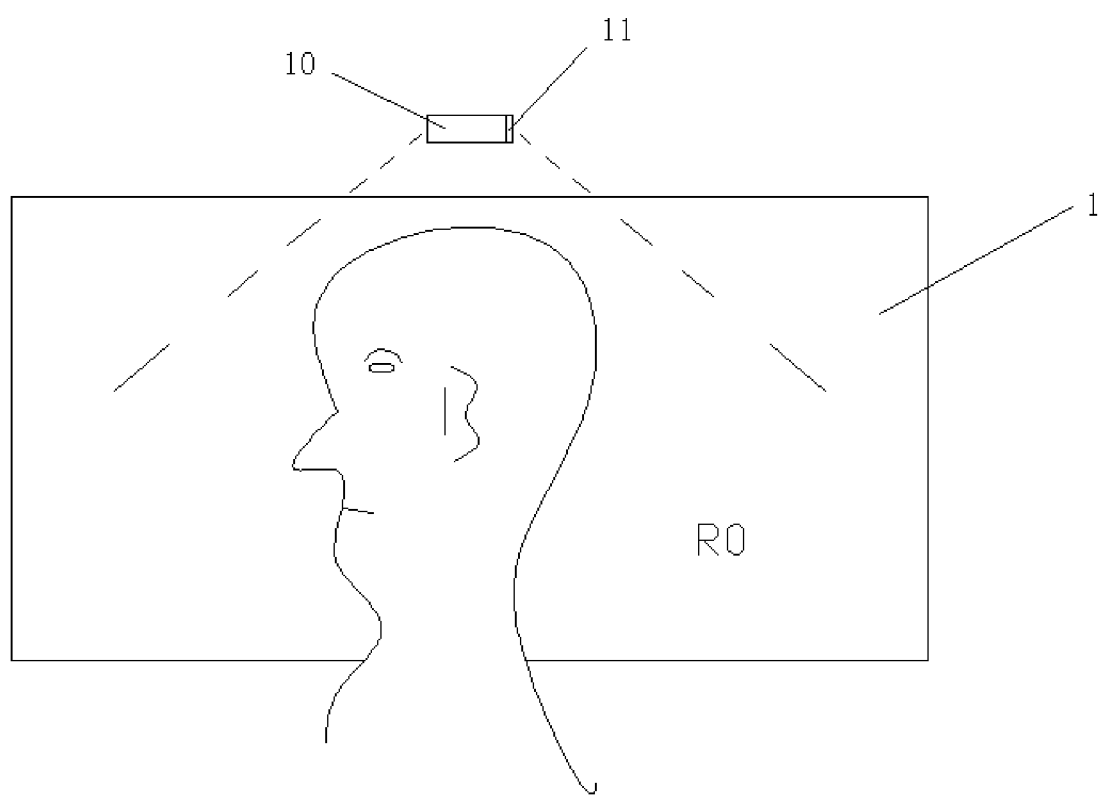
FIG. 5 is a top view showing a sleeper sleeping on his/her right side and his/her head is at the center of the main body (R0) according to Example One of the present disclosure.
Figure 6:
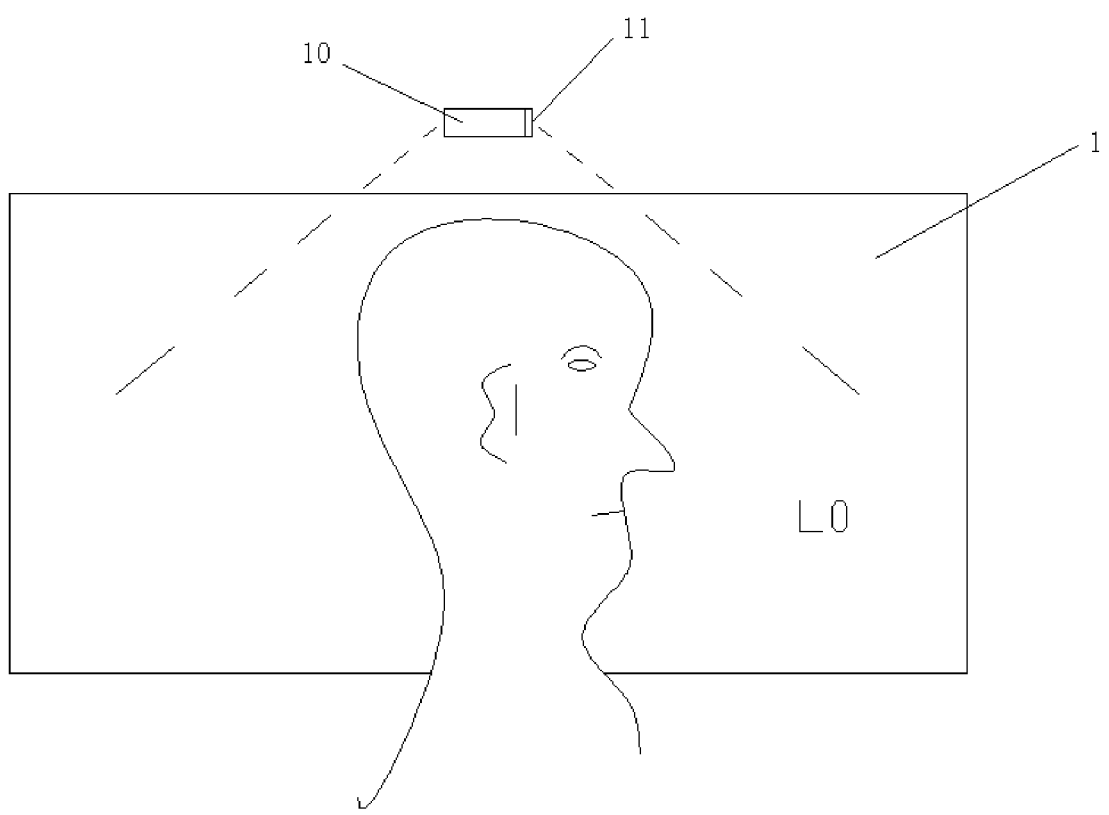
FIG. 6 is a top view showing a sleeper is sleeping on his/her left side and his/her head is at the center of the main body (L0) according to Example One of the present disclosure.
Figure 11A:
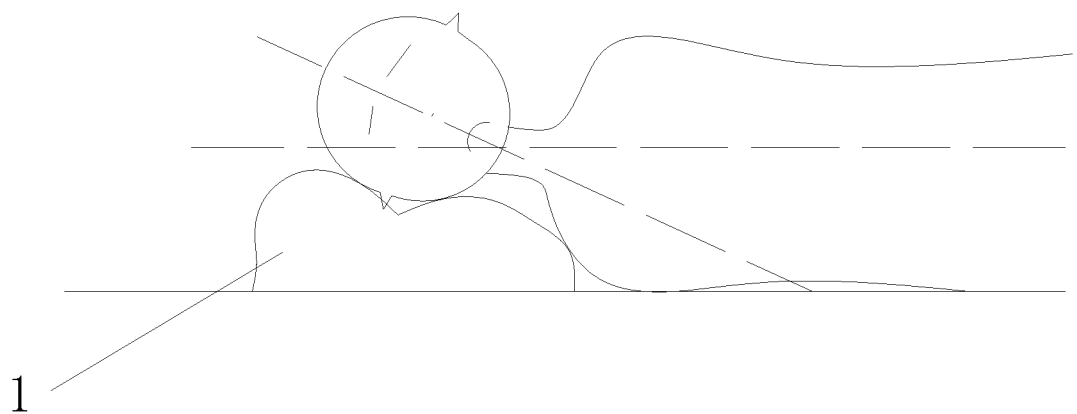
FIG. 11a is a schematic diagram illustrating a sleeper lying laterally with too high a head supporting area and too low a cervical spine supporting area according to Example One of the present disclosure.
Figure 11B:
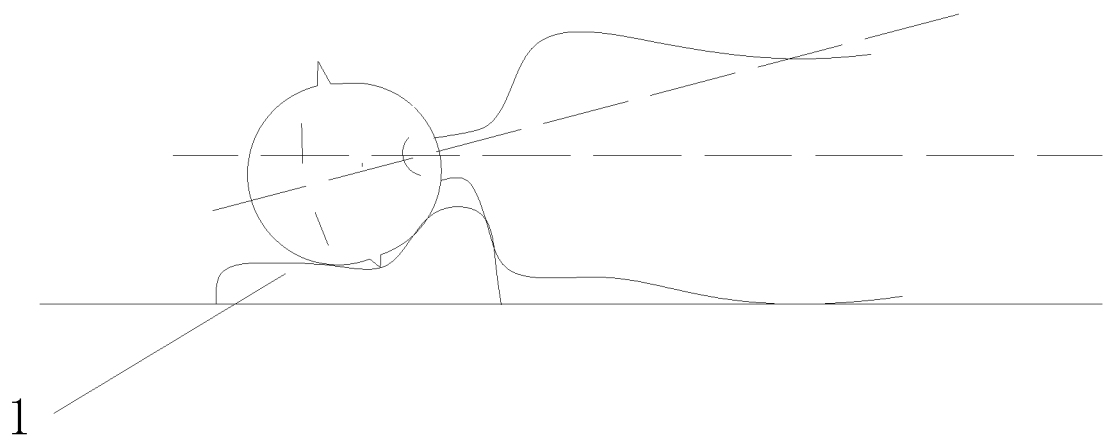
FIG. 11b is a schematic diagram illustrating a sleeper lying laterally with too low a head supporting area and too high a cervical spine supporting area according to Example One of the present disclosure.
Figure 11C:
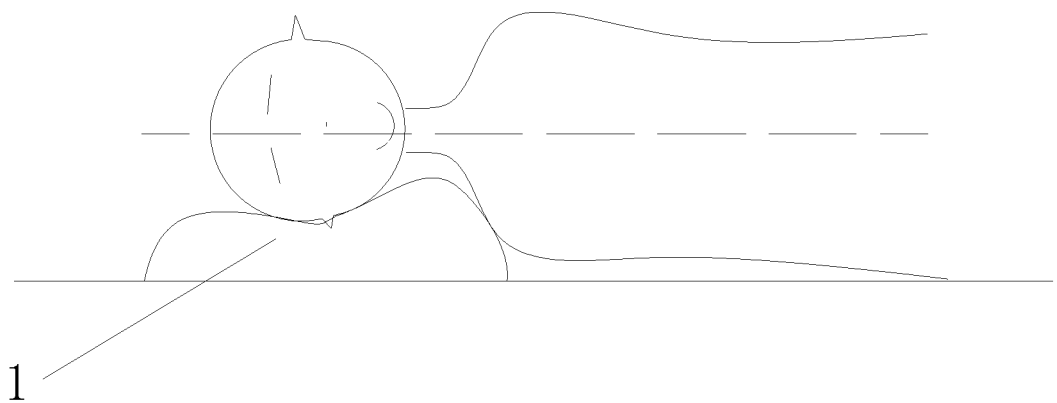
FIG. 11c is a schematic diagram illustrating a sleeper lying laterally with a head supporting area and a cervical spine supporting area of appropriate heights according to Example One of the present disclosure.

As shown in FIG. 11*a*, the head supporting area is too high, and the cervical spine supporting area is too low, so the axial line from the sleeper's vertex to the sleeper's chin is not on the same horizontal plane as the sleeper's cervical and thoracic spine. As shown in FIG. 11*b*, the head supporting area is too low, and the cervical spine supporting area is too high, so the axial line from the sleeper's vertex to the sleeper's chin is also not on the same horizontal plane as the sleeper's cervical and thoracic spine. As shown in FIG. 11*c*, each of the head supporting area and the cervical spine supporting area has an appropriate height, so the axial line from the sleeper's vertex to the sleeper's chin is on the same horizontal plane as the sleeper's cervical and thoracic spine. As shown in FIGS. 5 and 6, when the sensor 3 detects that the sleeper is lying laterally, the inflation-deflation mechanism 2 may drive the main body 1 to adjust the heights of the head and neck areas, maintaining the axial line from the sleeper's vertex to the sleeper's chin on the same horizontal plane as the sleeper's cervical and thoracic spine. When the sleeper is lying laterally, the accelerometer 12 will detect a change in the gradient, or the image sensor will sense an infrared image of the side of the person. The heights of the areas S of the head supporting area 7 and the areas C of the cervical spine supporting area 6 will be adjusted accordingly and automatically, so that the axial line from the sleeper's vertex to the sleeper's chin is on the same horizontal plane as the sleeper's cervical and thoracic spine. Each time the sleeper changes his/her sleeping posture, the accelerometer 12 will detect a change in the gradient, or the image sensor may sense a change in the infrared image After a period of observation (about 3-10 s), in which the physical motion of turning over has been accomplished, that is, after a series of static images have be acquired, the sensor 3 will update and transmit the still infrared image to the central information processor 4 for processing. Thereafter, each of the areas S of the head supporting area 7 and areas C of the cervical spine supporting area 6 will be adjusted to an optimal height.

Figure 7:
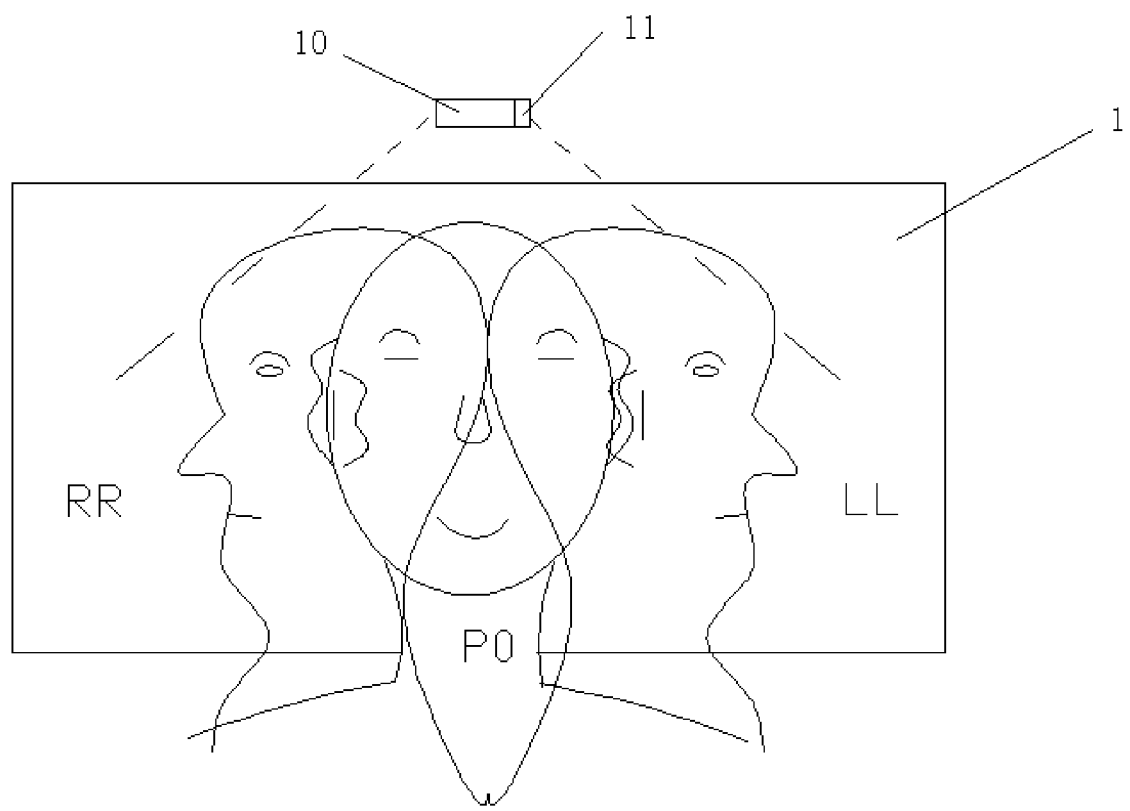
FIG. 7 is a top view showing a sleeper is sleeping on his/her right side and his/her head is on the right of the main body (RR), or a sleeper is sleeping on his/her left side and his/her head is on the left of the main body (LL), or a sleeper is lying supine and his/her head is at the center of the main body (P0) according to Example One of the present disclosure.
Figure 8:
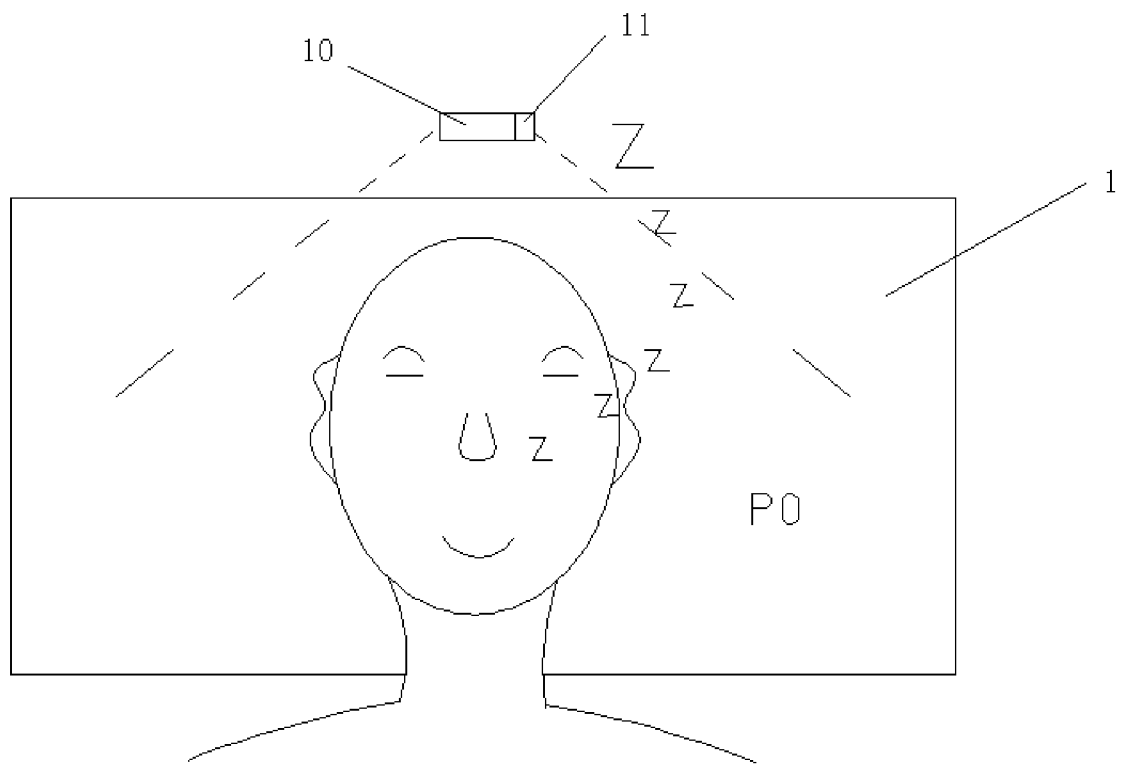
FIG. 8 is a top view showing a sleeper lying supine and snoring according to Example One of the present disclosure.

As shown in FIGS. 7 and 8, when the sensor 3 detects the sleeper is snoring or his/her respiratory rate falls below a predetermined value, and the sensor 3 detects that the sleeper is lying supine, the inflation-deflation mechanism 2 may drive the main body 1 to adjust the height of the head and neck areas, to facilitate the sleeper to change from lying supine to lying laterally. When a person is lying supine, it is easy to cause upper airway obstruction since the back of the tongue will tend to drop backwards. Snoring tends to occur when one sleeps on his/her back. When the sound sensor 11 detects that the sleeper is snoring, or the accelerometer 12 senses vibrations, this information may be processed by the central information processor 4 as information about snoring. If the image of the sleeper or the information sensed by the accelerometer 12 shows that the sleeper is lying supine (i.e., P0), a preset computer program may activate the three air bags 8 in the areas C to have different levels of inflation or deflation sequentially, to motivate the sleeper to change from lying supine to lying laterally (i.e., R0, RR or L0, LL), to improve the airway patency, and reduce or stop the snoring of the sleeper.

As shown in FIGS. 7 and 8, when the sensor 3 detects the sleeper is snoring or his/her respiratory rate falls below a predetermined value, and the sensor 3 detects that the sleeper is sleeping on his/her left side, the inflation-deflation mechanism 2 may drive the main body 1 to adjust the height of the head and neck areas, to facilitate the sleeper to change from sleeping on his/her left side to sleeping on his/her right side; and when the sensor 3 detects the sleeper is snoring or his/her respiratory rate falls below a predetermined value, and the sensor 3 detects that the sleeper is sleeping on his/her right side, the inflation-deflation mechanism 2 may drive the main body 1 to adjust the height of the head and neck areas, to facilitate the sleeper to change from sleeping on his/her right side to sleeping on his/her left side. That is, when the snorer is sleeping on his/her right side (i.e., R0 or RR), the device may motivate the sleeper to change to sleeping on his/her left side (i.e., L0 or LL), and when the snorer is sleeping on his/her left side (i.e., L0 or LL), the device may motivate the sleeper to change to sleeping on his/her right side (i.e., R0 or RR).

Preferably, the method may further include: controlling, by the central information processor, the inflation-deflation mechanism to withhold from intervening, preventing any movement of the main body from disturbing the sleeper, when the sensor detects that the sleeper is in deep sleep, and that each of blood oxygen saturation, breathing rate and heart rate of the sleeper falls within a predetermined range. When the accelerometer 12 and the image sensor 10 detects no change in the sleeping posture of the sleeper over a period of time, the central information processor 4 may determine that the sleeper is in a sleep state, and if each of the blood oxygen of the sleeper detected by the blood-oxygen measuring device, and the breath and heart rate of the sleeper detected by the accelerometer 12 falls within a predetermined range, the central information processor 4 will withhold the inflation-deflation mechanism from intervening.

Example Two

Both the image sensor 10 and the accelerometer 12 are used to detect the sleeping posture of the sleeper, and transmit information to the central information processor 4 in real time, so the sensor 3 in Example one includes the image sensor 10 and the accelerometer 12, both of which are applied in the adjustable pillow device to detect the sleeping posture of the sleeper. The adjustable pillow device in Example Two is different from the adjustable pillow device in Example One in that: the sensor 3 includes one of the image sensor 10 and the accelerometer 12, that is, either the image sensor 10 or the accelerometer 12 is applied in the adjustable pillow device, which can also achieve the detection of the sleeping posture of the sleeper.

Example Three

Figure 12:
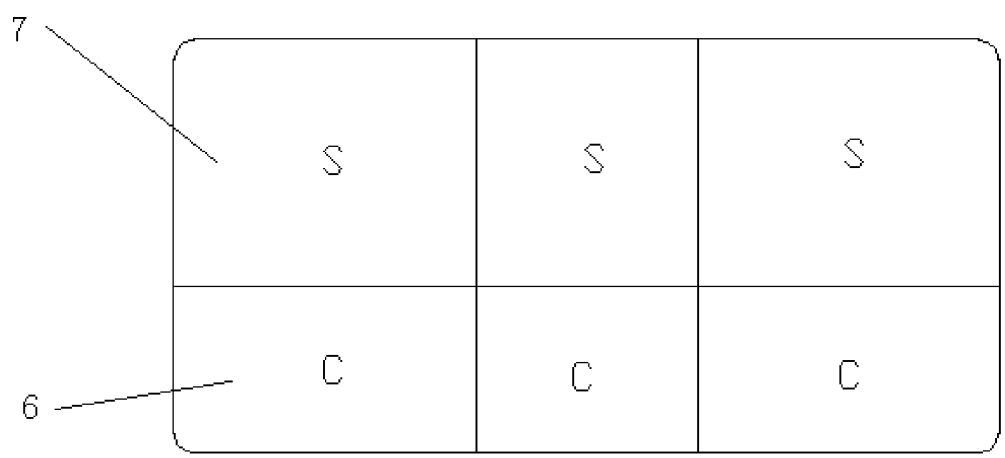
FIG. 12 is a top view of the main body according to Example Two of the present disclosure.

As shown in FIG. 12, the adjustable pillow device in Example Three is different from the adjustable pillow device in Example One in that: the cervical spine supporting area 6 is provided with three air bags 8 sequentially arranged along the length of the main body 1; and the head supporting area 7 is provided with three air bags 8 sequentially arranged along the length of the main body 1. The six air bags 8 may achieve a better adjustment to the head of the sleeper, and have a higher requirement on their sensitivity and production technology.

Each technical feature in the above embodiments can be combined in any way, and for the purpose of concise description, not all possible combinations of each technical feature in the above embodiments have been described, however, these combinations of each technical feature all belong to the scope of the present description as long as no contradiction exists.

The above embodiments have only shown certain modes of extrusion of the present disclosure, which is described more specifically and in detail, but it cannot be considered as limit to the scope of the present disclosure. It should be noted that, for those skilled in the art, this embodiments may have various variants and modifications without departing from the present inventive ideas and concept, all belong to the protection scope of the present disclosure. Thus, the protection scope of the present disclosure subjects to the attached claims

What is claimed is:

1. An adjustable pillow device, comprising:
   a main body, a height of the main body adjustable according to sleeping posture information and body figure data of a sleeper;
   an inflation-deflation mechanism, connected to the main body, and programmed to perform regional height adjustment of the main body;
   a sensor, programmed to collect and feed back the sleeping posture information about the sleeper; and
   a central information processor, connected to the sensor and to a control terminal of the inflation-deflation mechanism respectively, and configured to acquire the body figure data of the sleeper, receive the sleeping posture information from the sensor, and send an adjusting direction to the control terminal of the inflation-deflation mechanism based on both the sleeping posture information and the body figure data of the sleeper, the body figure data including collected dimensional data of at least one of a head, a neck, shoulders, and a chest of the sleeper,
   wherein the main body includes a cervical spine supporting area and a head supporting area, the cervical spine supporting area having a height higher than the head supporting area, and each of the cervical spine supporting area and the head supporting area is provided with at least one air bag,
   wherein the sensor includes an accelerometer configured to be located below the main body, or on the chest, back, hip, or head of the sleeper.

2. The adjustable pillow device of claim 1, wherein the cervical spine supporting area is provided with three air bags sequentially arranged along a length of the main body, and the head supporting area is provided with one air bag.

3. The adjustable pillow device of claim 1, wherein the cervical spine supporting area is provided with three air bags sequentially arranged along a length of the main body, and the head supporting area is provided with three air bags sequentially arranged along the length of the main body.

4. The adjustable pillow device of claim 1, wherein the inflation-deflation mechanism includes an air pump, and a pressure tubing connecting the air pump to the air bag, the air pump has a control terminal electrically connected to the central information processor, and the pressure tubing is provided with a switching valve electrically connected to the central information processor.

5. The adjustable pillow device of claim 4, wherein the air pump is a silent air pump.

6. The adjustable pillow device of claim 1, wherein the cervical spine supporting area and/or the head supporting area are provided with a temperature adjuster.

7. The adjustable pillow device of claim 1, further comprising plates arranged in the head supporting area and/or the cervical spine supporting area respectively, the plate arranged in the head supporting area is positioned away from the top of the head supporting area, and the plate arranged in the cervical spine supporting area is positioned away from the top of the cervical spine supporting area.

8. The adjustable pillow device of claim 4, wherein the central information processor and/or the air pump are arranged in a box with sound insulation properties.

9. The adjustable pillow device of claim 1, further comprising:
   an information storage device electrically connected to the central information processor;
   an information transmission mechanism electrically connected to the central information processor; and
   an environmental information collector electrically connected to the central information processor.

10. The adjustable pillow device of claim 1, wherein the sensor includes an image sensor to be installed above the head of the sleeper.

11. The adjustable pillow device of claim 1, wherein the sensor includes a sound sensor.

12. The adjustable pillow device of claim 1, wherein the sensor includes a blood-oxygen measuring device attached to a hand of the sleeper.

13. A pillow adjusting method of the adjustable pillow device of claim 1, comprising:
   collecting, by the sensor, sleeping posture information about the sleeper;
   receiving, by the central information processor, the sleeping posture information from the sensor, and sending an adjusting direction to the inflation-deflation mechanism based on the sleeping posture information and the body figure data of the sleeper; and
   performing, by the main body, regional height adjustment of the main body, directed by the inflation-deflation mechanism.

14. The pillow adjusting method of claim 13, wherein the adjusting includes:
   maintaining physiological curvature of the cervical spine of the sleeper by directing the main body to perform regional height adjustment via the inflation-deflation mechanism, when the sensor detects that the sleeper is lying supine.

15. The pillow adjusting method of claim 13, wherein the adjusting includes:
   maintaining that an axial line from the sleeper's vertex to the sleeper's chin is on the same horizontal plane as the sleeper's cervical and thoracic spine by directing the main body to perform regional height adjustment via the inflation-deflation mechanism, when the sensor detects that the sleeper is lying laterally.

16. The pillow adjusting method of claim 13, wherein the adjusting includes:
   facilitating the sleeper to change from lying supine to lying laterally by directing the main body to perform regional height adjustment via the inflation-deflation mechanism, when the sensor detects that the sleeper is snoring, with a respiratory rate below a predetermined value, and that the sleeper is lying supine.

17. The pillow adjusting method of claim 13, wherein the adjusting includes:
- facilitating the sleeper to change from sleeping on his/her left side to sleeping on his/her right side by directing the main body to perform regional height adjustment via the inflation-deflation mechanism, when the sensor detects that the sleeper is snoring, with a respiratory rate below a predetermined value, and that the sleeper is sleeping on his/her left side; and
- facilitating the sleeper to change from sleeping on his/her right side to sleeping on his/her left side by directing the main body to perform regional height adjustment via the inflation-deflation mechanism, when the sensor detects that the sleeper is snoring, with a respiratory rate below a predetermined value, and that the sleeper is sleeping on his/her right side.

18. The pillow adjusting method of claim 13, further comprising:
- controlling, by the central information processor, the inflation-deflation mechanism to withhold from intervening, when the sensor detects that the sleeper is asleep, and that each of blood oxygen saturation, breathing rate and heart rate of the sleeper falls within a predetermined range.

* * * * *